United States Patent [19]
Owolabi et al.

[11] Patent Number: 5,846,823
[45] Date of Patent: Dec. 8, 1998

[54] EXPRESSION OF HUMAN D4 DOPAMINE RECEPTORS IN STABLE CELL LINES

[75] Inventors: Joshua Owolabi, Brampton; Vikarna Rampersad, North York; Rajender Kamboj, Mississauga, all of Canada

[73] Assignee: Allelix Biopharmaceuticals, Mississauga, Canada

[21] Appl. No.: 623,471

[22] Filed: Mar. 28, 1996

Related U.S. Application Data

[63] Continuation-in-part of PCT/CA94/00538 filed Sep. 27, 1994, which is a continuation-in-part of Ser. No. 127,495, Sep. 28, 1993, abandoned.

[51] Int. Cl.$^6$ ..................................................... C12N 5/16
[52] U.S. Cl. ........................................... 435/325; 435/361
[58] Field of Search .......................... 435/7.1, 7.2, 69.1, 435/252.3, 320.1, 325; 530/350; 536/23.4

[56] References Cited

U.S. PATENT DOCUMENTS 5,242,822   9/1993   Marulla et al. ....................... 435/252.3

FOREIGN PATENT DOCUMENTS

WO 9210571   6/1992   WIPO .
WO 94 03602   2/1994   WIPO .

OTHER PUBLICATIONS

Civelli et al., "Molecular diversity of the dopamine receptors" Annu Rev Pharmacol Toxicol, 1993, 32:281.
Dearry et al "Molecular cloning and expression of the gene for a human D1 dopamine receptor" Nature, 1990, 347:72.
Grandy et al "Cloning of the cDNA and gene for a human D2 dopamine receptor" Proc Natl Acad Sci, 1989, 86:9762.
Giros et al "cDNA cloning fo the human dopaminergic D3 receptor and chromosome identification" C R Acad Sci Paris, 1990, 311:501.
Kane et al "Clozapine for the treatment–resistant schizophrenic" Arch Gen Psychiatry, 1988, 45:789.
Kozak et al "Point mutations define a sequence flanking the AUG initiator condon that modulates translation by eukaryotic ribosomes" Cell, 1996, 44:283.
O'Dowd et al "Structures of dopamine receptors" J Neurochemistry, 1993, 60(3):804.
Salomon et al "A highly sensitive adenylate cycalse assay" Anal Biochem, 1974,58:541.
Sanger et al "DNA sequencing with chain–terminating inhibitors" Proc Natl Acad Sci, 1977, 74(12):5463.
Schwartz et al "Multiple dopamine receptors as molecular targets for antipsychotics" Int Acad Biomed Drug Res. Basel, Karger, 1993, vol. 4 pp. 1–14.

Seeman et al "Dopamine D4 receptors bind inactive (+)–aporphines, suggesting neuroleptic role. Sulpride not stereoselective" Eur J Pharm, 1993, 233:173.
Seeman et al "Dopamine receptor sequences" Neuropsychopharmacology, 1992 7(4):261.
Strange "Interesting times for dopamine receptors" Trends in Neurosciences, 1991, 14(2):43.
Van Tol et al "Multiple dopamine D4 receptor variants in the human population" Nature, 1992, 358:149.
Van Tole et al "Cloning of the gene for a human dopamine D4 receptor with high affinity for the antipsychotic clozapine" Nature, 1991, 350:610.
Bouvier et al Society for Neuroscience abstracts, 1993, 19:735 no. 302.15 "Expression of functional $D_4$ $D_2$ dopamine receptors using vaccinia virus as an expression system".
Chio et al Society for Neuroscience abstracts, 1993, 19:735 No. 302.17 "Activation of human D4 receptors heterologously expressed in CHO–K1 cells and HEK 293 cells".
Mills et al Society for Neuroscience abstracts, 1993, 19:734 No. 302.12 "Characterisation of functional activity of dopamine ligands at human recombinant dopamine $D_4$ receptors".
Tritch et al Society for Neuroscience abstracts, 1993, 19:735 No. 302.16 "The human dopamine $D_4$ receptor: construction and characterization of stable mammalian cell lines expressing a synthetic $D_4$ cDNA clone".
Chio et al FASEB Journal, 1993 vol. 7, No. 4, p. A693 "Expression of a gene for the dopamine D4 receptor".
Chio et al Journal of Biological Chem., vol. 269, No. 6, 1994, pp. 11813–11819 "D4 dopamine receptor–mediated signaling events determined in transfected Chinese hamster ovary cells".
McHale et al FEBS Letters, 1994, vol. 345, pp. 147–150 "Expression and functional characterisation of a synthetic version of the human D4 dopamine receptor in a stable human cell line".
Hausdorff et al Biochemistry, 1991, 30:3341–3346 "Functional characterization of a Minimal $K^+$Channel Expressed from a Synthetic Gene".
Claudio et al Science, 1987, vol. 239, pp. 1688–1694 "Genetic Reconstruction of Functional Acetylcholine Receptor Channels in Mouse Fibrobalsts".
Kozak Nuleic Acids Research, 1987, vol. 15, No. 20, pp. 8125–8132 "An analysis of 5'–noncoding sequences from 699 vertebrate messenger RNAs".

*Primary Examiner*—John Ulm
*Attorney, Agent, or Firm*—Ridout & Maybee

[57] ABSTRACT

Cell lines that stably incorporate human $D_4$ receptor-encoding DNA are provided which are particularly useful in procedures for screening compounds for potential antipsychotic activity.

1 Claim, 6 Drawing Sheets

|  |  |  | REPEAT 1 |
|---|---|---|---|
| SEQ ID NO:6 | D4.2... | ACG CC | A CCC GCG CCC GCG CTC CCC CAG GAC CCC GGC CCC TGC GGC CCC GAC TGT GCG CC |
| SEQ ID NO:7 | D4.4... | ACG CC | A CCC GCG CCC GCG CTC CCC CAG GAC CCC TGC GGC CCC GAC TGT GCG CC |
| SEQ ID NO:8 | D4.7... | ACG CC | A CCC GCG CCC GCG CTC CCC CAG GAC CCC TGC GGC CCC GAC TGT GCG CC |

REPEAT 2
C CCC GCG CCC GGC CTT CCC CGG GGT CCC TGC GGC CCC GAC TGT GCG CC
C CCC GCG CCC GGC CTT CCC CGG GGT CCC TGC GGC CCC GAC TGT GCG CC

REPEAT 3

REPEAT 4
C GCC GCG CCC GGC CTC CCC CCG GAC CCC TGC GGC CCC GAC TGT GCG CC
C CCC GCG CCC GGC CTC CCC CCG CAG GAC CCC TGC GGC CCC GAC TGT GCG CC

REPEAT 5
C CCC GCG CCC GGC CTT CCC CGG GGT CCC TGC GGC CCC GAC TGT GCG CC

REPEAT 6
C GCC GCG CCC AGC CTC CCC CAG GAC CCC TGC GGC CCC GAC TGT GCG CC
C CCC GCG CCC GGC CTC CCC CAG GAC CCC TGC GGC CCC GAC TGT GCG CC

REPEAT 7
C CCC GCG CCC GGC CTC CCC CCG GAC CCC TGC GGC TCC AAC TGT GCT CC | C CCC...D4.2
C CCC GCG CCC GGC CTC CCC CCG GAC CCC TGC GGC TCC AAC TGT GCT CC | C CCC...D4.4
C CCC GCG CCC GGC CTC CCC CCG GAC CCC TGC GGC TCC AAC TGT GCT CC | C CCC...D4.7

FIG. 2B $D_4$ NUCLEOTIDE SEQUENCE

PLASMID #1

5 AAGCTT GCC GCC ACC ATG G---$D_{4.2}$---TGC TGA GCC GGGCA...native 3

SEQ ID NO:9　　　　　　　　　　　　　SEQ ID NO:10

PLASMID #2

5 AAGCTT GCC GCC ACC ATG G---$D_{4.2}$---TGC TGA GCC GGGCA AAGCTT 3

SEQ ID NO:9　　　　　　　　　　　　　SEQ ID NO:11

PLASMID #4

5 GGG CGC GCC ATG G---$D_{4.2}$---TGC TGA GCC GGGCA...native 3

SEQ ID NO:12　　　　　　　　　　　　SEQ ID NO:10

EXPRESSION OF HUMAN D4 DOPAMINE RECEPTORS IN STABLE CELL LINES

CROSS REFERENCE OF RELATED APPLICATIONS

This application is a continuation-in-part of international patent application PCT/CA94/00538 filed Sep. 27, 1994, which in turn is a continuation-in-part of U.S. application Ser. No. 08/127,495 filed Sep. 28, 1993, now abandoned.

FIELD OF THE INVENTION

The present invention relates to the application of recombinant DNA technology in the field of neuroscience. More particularly, the invention relates to cells transformed to produce mammalian dopamine receptors, and to the construction and use of such cells particularly for ligand screening purposes.

BACKGROUND OF THE INVENTION

The family of G protein-coupled dopamine receptors currently comprises the $D_1$, $D_2$, $D_3$, $D_4$ and $D_5$ subtypes as described in Nature, 1990, 347:72; Pro. Natl. Acad. Sci., USA, 1989, 86:9762; C.R. Acad. Sci. Paris, 1990, 311:501; Nature, 1991, 350:610; and Nature, 1991, 350:614. It is theorized that aberrant interaction between these receptors and the neurotransmitter, dopamine, may be responsible for certain disorders including Parkinson's disease and schizophrenia. Of particular interest is the finding that the antipsychotic drug, clozapine, which is effective in the treatment of schizophrenia (Arch. Gen. Psychiatry, 1988, 45:789), binds selectively to the $D_4$ receptor (Nature, 1991, 350:610). This suggests that determination of $D_4$ receptor binding properties is a useful step in identifying other effective anti-psychotic drugs.

Preliminary pharmacological characterization of the $D_4$ receptor has been performed. DNA coding for human forms of the dopamine $D_4$ receptor have been cloned and transiently expressed in COS cells as reported in Nature, 1991, 350:610 and in Nature, 1992, 358:149. These cells, and membrane preparations derived from them, constitute a useful but temporary substrate for screening chemical compounds for specific $D_4$ receptor-binding properties. Particularly, cells that are transiently transfected do not integrate the receptor-encoding DNA, and thus do not stably express that DNA on continuous passage. Transient cells are therefore not a regenerable source of receptor, and must therefore be constructed in batches as required. This is not only time consuming but can also introduce unwanted variation in receptor expression, integrity and function, and hence in experimental results.

To screen chemical compounds for specific $D_4$ receptor-binding in an efficient and consistent manner, cell lines which genomically incorporate human $D_4$ receptor-encoding DNA, and which express that DNA stably and efficiently to yield functional receptor, are desirable. It is an object of the present invention to provide such a stable $D_4$ receptor-expressing cell line.

SUMMARY OF THE INVENTION

In one of its aspects, the present invention provides a stable cell line having integrated genomically and expressibly therein a DNA molecule that encodes a human dopamine $D_4$ receptor. Such cells constitute a continuous and homogeneous source of functional $D_4$ receptor, for use in screening programs aimed at identifying drug candidates, particularly anti-psychotic drugs. In a related aspect, the invention provides membrane preparations derived from such cells, for use in human D4 receptor-binding assays.

In another aspect of the present invention, there is provided a method for identifying $D_4$ ligands within a chemical compound library, comprising the step of incubating a compound with stable cells encoding the $D_4$ receptor, or with membrane preparations derived from these cells, and then determining the extent of receptor/compound binding.

For use in constructing cells that have been stably transfected with DNA coding for the human $D_4$ receptor, the invention further provides a recombinant DNA construct comprising a human D4 receptor-encoding DNA molecule that is tailored at one or both of its 5' and 3' non-coding flanks. In one preferred embodiment, the DNA molecule incorporates at its 5' end a translation-enhancing sequence that is modified relative to the native translation-enhancing sequence. In other embodiments, the transcriptional controls at one or both of the 5' and 3' ends of the D4 receptor gene are removed, and replaced by heterologous, vector-encoded expression controls.

Other aspects of the present invention will become apparent from the following detailed description, and from the accompanying drawings, in which:

BRIEF REFERENCE TO THE DRAWINGS

DETAILED DESCRIPTION AND PREFERRED EMBODIMENTS

The present invention provides a regenerable source of functional human dopamine $D_4$ receptor in the form of stable cell lines. Cells having human $D_4$ receptor-encoding DNA integrated genomically therein are referred to herein as "stable". Unlike transiently transformed $D_4$ receptor-expressing cells reported in the literature, which harbour the receptor-encoding DNA as plasmids that replicate autonomously, the stable cells of the present invention carry the $D_4$ receptor-encoding DNA as genomically integrated genetic material that is stably inherited through cell generations, i.e. on continuous passage. The present cells thus provide a regenerable source of homogeneous $D_4$ receptor material for drug screening programs.

Figure 1:
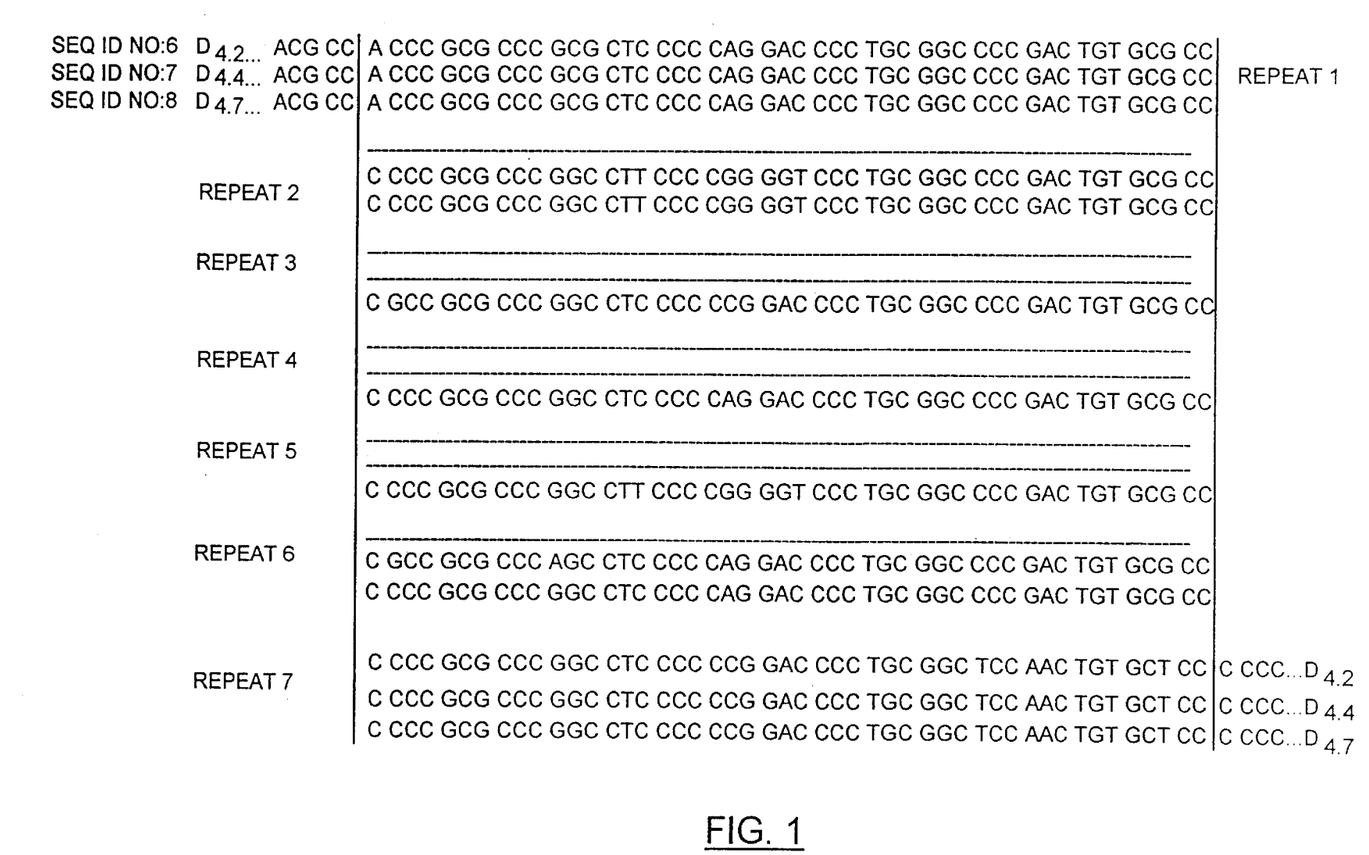
FIG. 1 provides the nucleotide sequence of non-overlapping regions of three forms of the $D_4$ receptor, namely the $D_{4.2}$ (SEQ ID NO:6), $D_{4.4}$ (SEQ ID NO:7) and the $D_{4.7}$ (SEQ ID NO:8) forms.

As used herein, the term "human dopamine $D_4$ receptor" refers to human $D_4$ receptor proteins which exhibit selective clozapine binding, including those $D_4$ receptor proteins containing sequence repeats as illustrated in FIG. 1 (SEQ ID NO:6–NO:8), e.g. the $D_{4.2}$, $D_{4.4}$ and $D_{4.7}$ receptors, as well as natural allelic variations of human $D_4$ receptor proteins. The term "selective clozapine binding" is meant to refer to the greater binding affinity exhibited by clozapine for human $D_4$ receptors relative to that exhibited by clozapine for other known human dopamine receptors, particularly the $D_1$, $D_2$, $D_3$ and $D_5$ receptors.

In the present specification, a dopamine receptor is said to be "functional" if a cellular host producing it exhibits clozapine binding, as determined using assays of conventional design, such as the assays described in Nature, 1991, 350:610, and described in greater detail herein in the specific examples.

For use in receptor binding assays, it is desirable to construct by application of genetic engineering techniques a mammalian cell line that produces the $D_4$ receptor in functional form as a heterologous product. The construction of such cell lines is achieved by introducing into a selected host cell a recombinant DNA construct in which DNA coding for the human $D_4$ receptor is associated with expression controlling elements that are functional in the selected host to drive expression of the receptor-encoding DNA, and thus elaborate the desired $D_4$ receptor protein. The particular cell type selected to serve as host for production of the human $D_4$ receptor can be any of several cell types currently available in the art, including both prokaryotic and eukaryotic, but should not of course be a cell type that in its natural state elaborates a surface receptor that can bind dopamine, and so confuses the assay results sought from the engineered cell line. Conveniently, such problems are avoided by selecting as host a non-neuronal cell type. It will be appreciated that neuronal-type cells may nevertheless serve as expression hosts, provided that "background" binding to the test ligand is accounted for in the assay results.

According to one embodiment of the present invention, the cell line selected to serve as host for $D_4$ production is a mammalian cell line derived from non-neuronal tissue. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney (HEK) cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available. Any one of these systems can be exploited to drive expression of the $D_4$ receptor-encoding DNA. These systems, available typically in the form of plasmidic vectors, incorporate expression cassettes the functional components of which include DNA constituting expression controlling sequences, e.g., transcription initiating elements, which are host-recognized and enable expression of the receptor-encoding DNA when linked 5' thereof. Such receptor-encoding DNA is referred to herein as being incorporated "expressibly" into the system, and incorporated "expressibly" in a cell once successful expression from a cell is achieved. These systems further incorporate DNA sequences, e.g., transcription terminating elements, which terminate expression when linked 3' of the receptor-encoding region. Thus, for expression in the selected mammalian cell host, there is generated a recombinant DNA expression construct in which the receptor-encoding DNA is linked with expression controlling DNA sequences recognized by the host, and which include a region 5' of the receptor-encoding DNA to drive expression, and a 3' region to terminate expression.

Included among the various recombinant DNA expression systems that can be used to achieve mammalian cell expression of the receptor-encoding DNA are those that exploit promoters of viruses that infect mammalian cells, such as the promoter from cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters, including those isolated from Drosophila which are regulated by temperature, as well as mammalian gene promoters such as those regulated by heavy metals, i.e. the metalothionein gene promoter, and other steroid-inducible promoters.

The plasmidic vector system harbouring the expression construct typically incorporates a marker to enable selection of stably transformed recombinant cells. The marker generally comprises a gene conferring some survival advantage on the transformants allowing for the selective growth of successful transformants in a chosen medium. For example, common gene markers include genes which code for resistance to specific drugs, such as tetracycline, ampicillin and neomycin.

For incorporation into the recombinant DNA expression vector, DNA coding for the desired $D_4$ receptor, e.g. the $D_{4.2}$ receptor or a pharmacologically related variant thereof, can be obtained by applying appropriately selected techniques of gene isolation or gene synthesis. Conveniently, and as described in more detail in the examples herein, the $D_{4.2}$ receptor, and the $D_{4.4}$ and $D_{4.7}$ variants thereof, can be isolated from commercially available human brain cDNA libraries, preferably cDNA libraries established from fresh human cerebellum or hippocampus tissue. Alternatively, such cDNA can be obtained by de novo construction of a cDNA library, using techniques well established for this purpose.

Having herein provided the nucleotide sequence of the $D_4$ receptor, it will be appreciated that automated techniques of gene synthesis and/or amplification can be performed to generate $D_4$ DNA. In this case, because of the length of the $D_4$ receptor-encoding DNA, application of automated synthesis may require staged gene construction in which regions of the gene up to about 300 nucleotides in length are synthesized individually and then ligated in correct succession via designed overlaps. Individually synthesized gene regions can then be amplified by PCR.

Preferentially, long oligonucleotides are synthesized, for example, fragments of about 300 nucleotides in length. In this method, the crude oligonucleotide mixture contains not only a very small amount of the correct full-length oligonucleotide of interest, but also large quantities of shorter-length so-called failure sequences which significantly contaminate the oligonucleotide mixture. However, the correct, full-length oligonucleotide material may be amplified by application of the technique of PCR, utilizing priming sequences corresponding to the ends of the full-length template oligonucleotide sequence, in order to facilitate separation thereof from the contaminating sequences. The amplified, full-length fragments may then be sequentially assembled as described above, except of course that many fewer fragments and ligations will now be required.

With appropriate template DNA in hand, the technique of PCR amplification may be used to directly generate all or part of the final gene. In this case, primers are synthesized which will prime the PCR amplification of the final product, either in one piece, or in several pieces that may subsequently be ligated together via step-wise ligation of blunt ended, amplified DNA fragments, or preferentially via step-wise ligation of fragments containing naturally occurring restriction endonuclease sites. Both cDNA or genomic DNA are suitable as templates for PCR amplification. The former may be obtained from a number of sources including commercially available cDNA libraries, single- or double-stranded cDNA, or cDNA constructed from isolated messenger RNA from a human brain. Human genomic DNA may also be used as a template for the PCR-based amplification of the gene; however, the gene sequence of such genomic DNA may contain unwanted intervening sequences.

Figure 5:
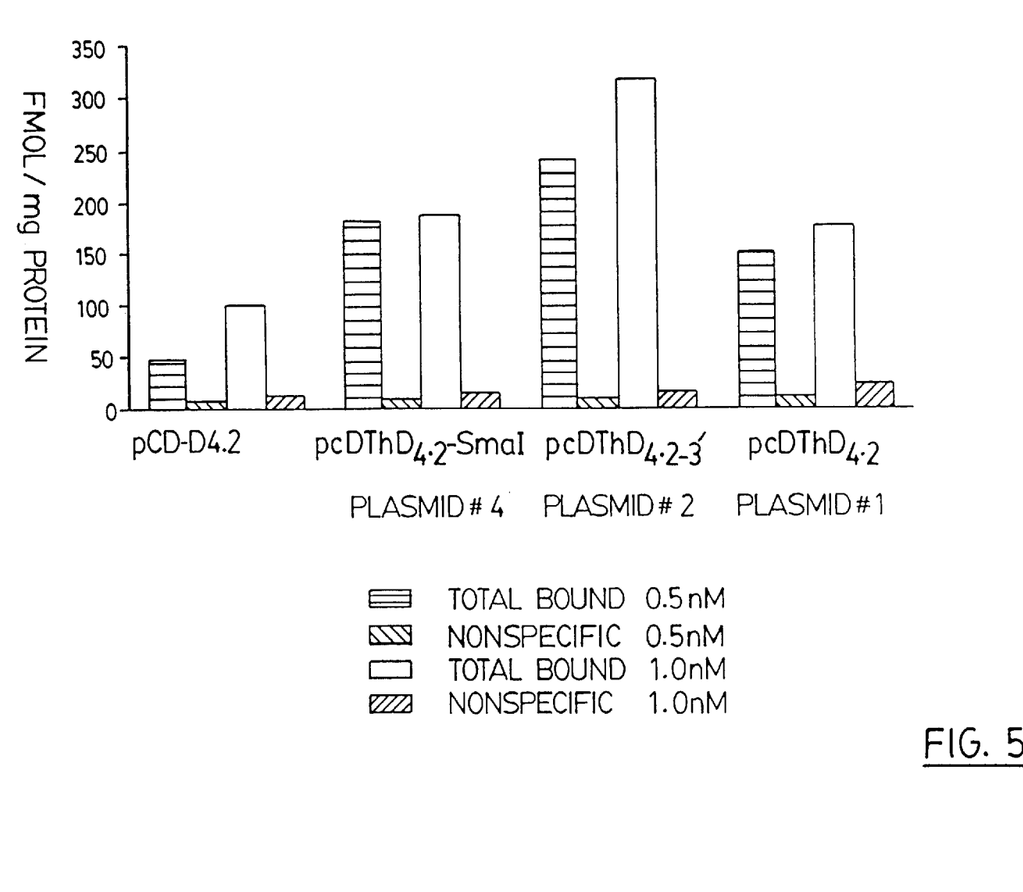
FIG. 5 is a comparison of the expression of modified forms of the $D_4$ receptor.

According to one aspect of the invention, it has been found that stable cell lines result reliably and reproducibly when the 5' and 3' untranslated regions associated natively with the D4 receptor-encoding DNA are replaced and/or modified. Particularly, it is preferable to use transcriptional controls offered by plasmidic vectors appropriate for the chosen host, rather than the transcriptional controls, i.e., the promoter and terminator, associated with the endogenous D4 receptor-encoding DNA. Also, it is desirable to retain or modify the translational controls associated with the native D4 receptor-encoding DNA. It is likely that these structural modifications correct instability inherent in the native D4 receptor DNA, particularly the cDNA, and thereby permit not only the genomic integration and stable inheritance of the DNA, but also the elevated levels of receptor protein expression observed in stable transfectants. Cells transformed with plasmidic expression vectors harbouring such modified $D_4$ receptor encoding DNA have been found to express substantially larger amounts of human $D_4$ receptor (FIG. 5).

More particularly, according to one embodiment of the present invention, the 5' untranslated region associated with the native $D_4$ receptor-encoding DNA is eliminated, by truncating the gene at a location 5' of, e.g. from 1 up to 50 bases upstream of, its native translation enhancing sequence, using conventional methods of restriction enzyme digestion and ligation. In a particularly preferred embodiment, the 5' truncated receptor-encoding DNA is further altered to incorporate a heterologous translation-enhancing sequence. By "heterologous" is meant a sequence that is not native to the $D_4$ receptor-encoding gene. Further, by "translation-enhancing sequence" is meant the 5' sequence which is required for translation to occur, and includes the translation initiation codon, i.e. ATG.

Heterologous sequences useful as translation-enhancing sequences are represented generally as follows:

-NN-P-NN-ATG-G- wherein A, T, G and C represent adenine, thymine, guanine and cytosine, respectively, N represents any one of adenine, thymine, guanine and cytosine, and P represents one of the purines, adenine or guanine (Cell, 1986, 44:283). A preferred version of this general translation-enhancing sequence is represented as follows:

-CC-ACC-ATG-G-

In a specific embodiment of the present invention, this sequence has been modified to provide as the most preferred translation-enhancing sequence for expression of the $D_4$ receptor, the following sequence (SEQ ID NO:1):

-GCC-GCC-ACC-ATG-G-

Figure 3:
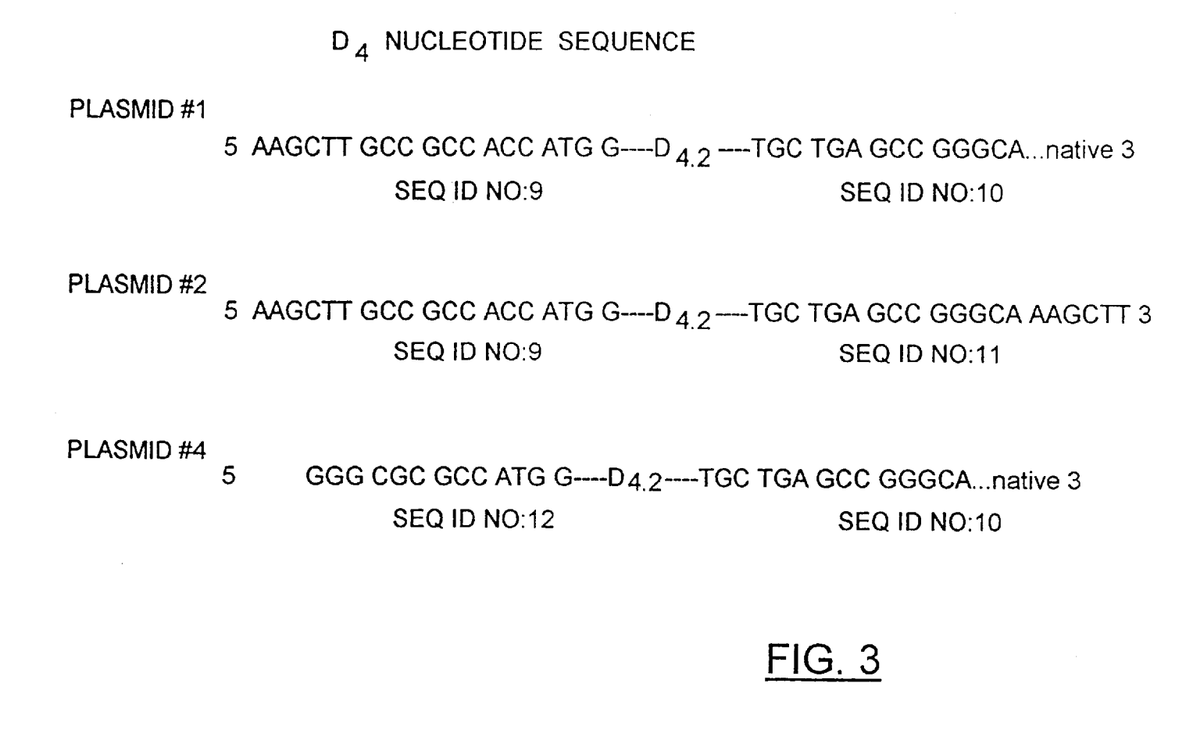
FIG. 3 illustrates preferred nucleotide sequences of the 5' (SEQ ID NO:9 and SEQ ID NO:12) and 3' (SEQ ID NO:10 and SEQ ID NO:11) non-coding regions of the $D_4$ receptor.

In another embodiment of the present invention, the $D_4$ receptor-encoding DNA is incorporated on the plasmidic vector without the transcriptional terminating sequences associated naturally with its 3' end. Desirably retained at the 3' end of the receptor-encoding DNA is the translational stop codon and at least about 5 bases, preferably 10 bases, further downstream thereof, the additional bases serving to faciliate the signalling of a translational stop. Elimination and modification in this manner of expression controlling elements associated naturally with human D4 receptor-encoding DNA has been found to provide even greater increases in the levels of product expression. As noted above, these manipulations are done most conveniently by applying standard methods of DNA manipulation to cDNA coding for the chosen human D4 receptor. Restriction enzyme digestion followed by ligation, may be used in order to effect such a modification to the $D_4$-encoding DNA. For further clarity, FIG. 3 illustrates the preferred modifications to be made to the 5' (SEQ ID NO:9, SEQ ID NO:12) and 3' (SEQ ID NO:10, SEQ ID NO:11) non-coding regions of the $D_4$ DNA sequence to provide increased levels of expression.

In its tailored form, the human D4 receptor-encoding DNA is necessarily incorporated on the chosen expression plasmid so that its expression is controlled by plasmid-borne expression/transcriptional controls, in accordance with standard practise. Once obtained, the receptor-encoding DNA is incorporated on the expression vector, selected host cells are transfected therewith using conventional procedures, such as DNA-mediated transformation including calcium phosphate precipitation, protoplast fusion, microinjection, lipofection and electroporation. Stable transfectants are then selected in culture and by procedures including Southern blot analysis, and propagated in media appropriate for the chosen host strain.

For use in screening assays, stable cell lines expressing the receptor-encoding DNA can be stored frozen for later use. Alternatively, membrane preparations can be derived from such cells to provide a more convenient substrate for the ligand binding experiments. To prepare membrane preparations for screening purposes, i.e. ligand binding experiments, frozen intact cells are homogenized while in cold water suspension and a membrane pellet is collected following centrifugation. The membranes may then be used as such in the ligand binding assays, or stored in lyophilized form for later use. Alternatively, intact, fresh cells, harvested about two days following fresh plating in conventional media, can be used for ligand binding assays by the same methods as used for membrane preparations. In this case, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human $D_4$ receptor of the invention is performed typically using a predetermined amount of cell-derived membrane (measured for example by protein determination). A suitable amount of cell-derived membrane is from about 25 $\mu$g to 100 $\mu$g. Generally, competitive binding assays will be useful to evaluate the affinity of a test compound relative to a known $D_4$ ligand, for example spiperone or dopamine. This competitive binding assay is performed by incubating the membrane preparation with radiolabelled ligand, for example [$^3$H]-spiperone, in the presence of various concentrations of unlabelled test compound. Following incubation, either displaced or bound radiolabelled spiperone can be recovered and measured to determine the relative binding affinities of the test compound and spiperone for the particular receptor used as substrate. In this way, the affinities of various compounds for the human dopamine $D_4$ receptors can be measured.

In another aspect of the present invention, candidate ligands may be screened using a functional assay to determine their ability to modulate $D_4$ receptor activity. Such a functional assay provides a means to differentiate antagonistic ligands from agonistic ligands. Thus, a functional ligand screening technique is provided comprising the steps of subjecting $D_4$ receptor-expressing cells in accordance with the present invention to adenylyl cyclase stimulant treatment, e.g. with forskolin, followed by incubation with a candidate ligand and a labelled substrate for adenylyl cyclase, e.g. $[\alpha^{32}P]ATP$, and then determining the extent of ligand-induced adenylyl cyclase activity, e.g. by determining the conversion of $[\alpha^{32}P]ATP$ to $[^{32}P]cAMP$. Techniques such as those described in Salomon et al. in Anal. Biochem., 1974, 58:541 are useful to determine the conversion of ATP to cAMP.

Embodiments of the present invention are described in the following specific examples which are not to be construed as limiting.

EXAMPLE 1

Preparation of Vectors containing $D_4$ Receptor DNA

Figure 2A:
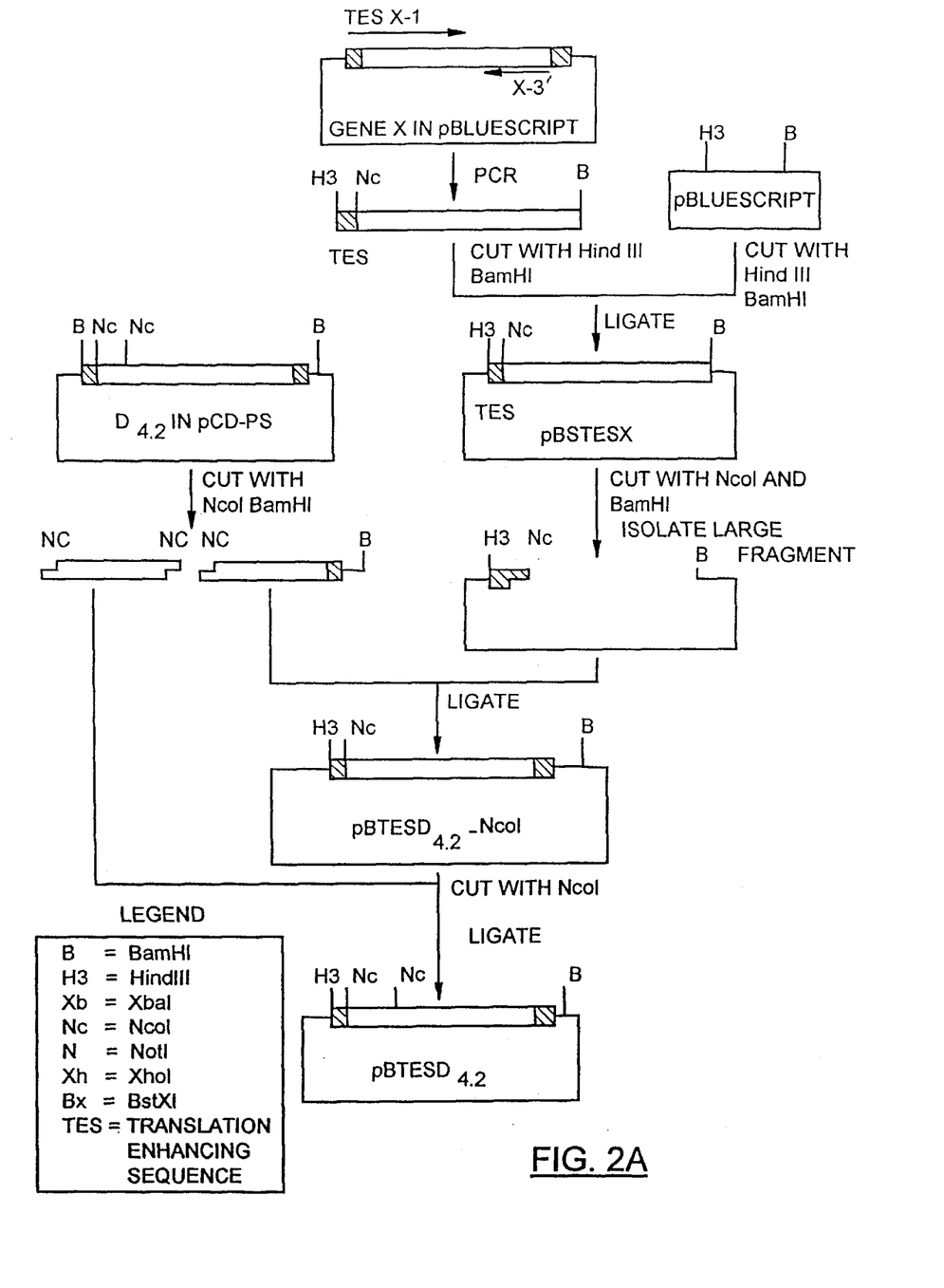
FIGS. 2a and 2b illustrate with linear plasmid maps the strategy used to construct expression vectors harbouring a $D_4$ DNA sequence.
Figure 2B:
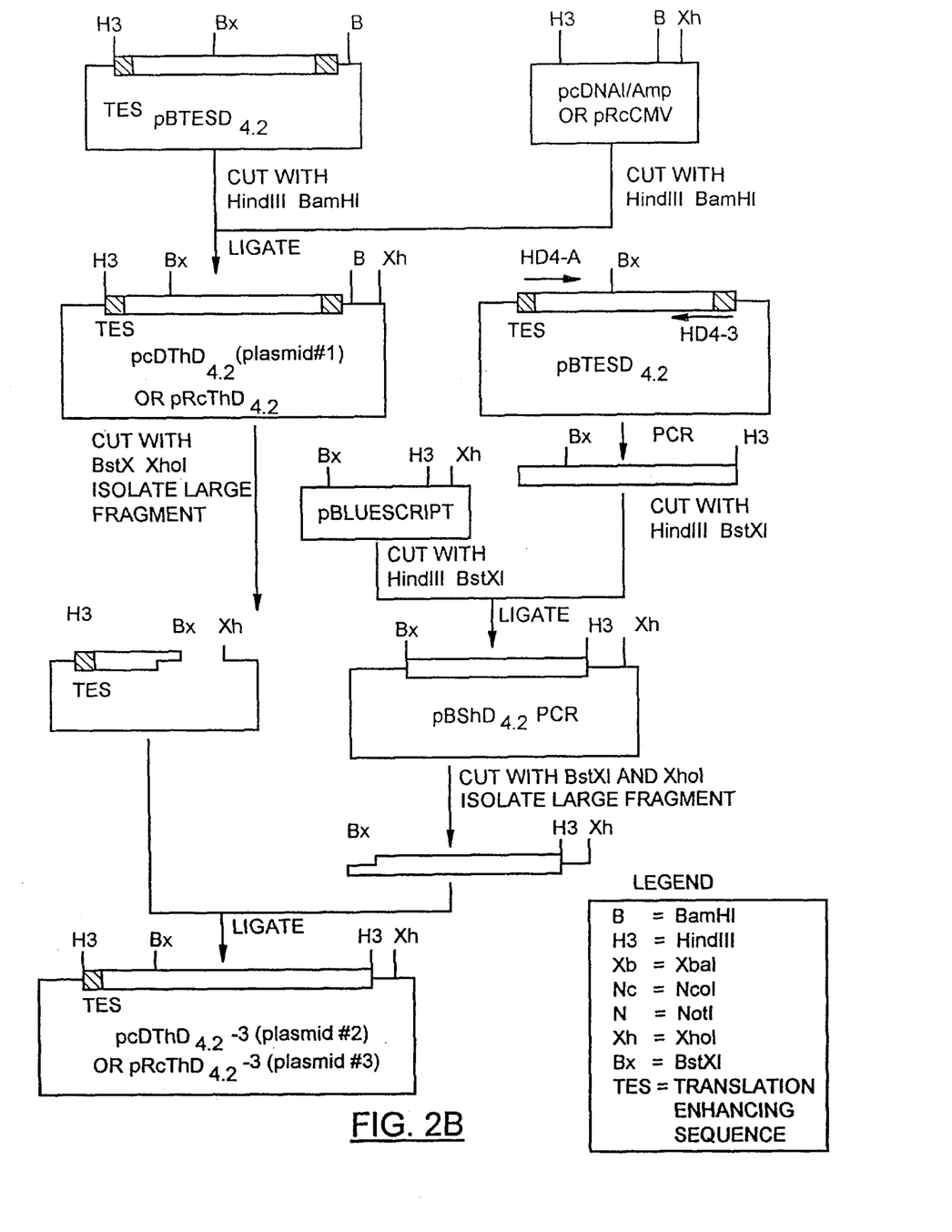

The following description provides the steps taken to prepare $D_4$ receptor-expressing cell lines in accordance with the present invention. FIGS. 2a and 2b illustrate the digestion and plasmid ligation products of steps 1–9.

Vector containing $D_4$ Receptor having a heterologous 5' translation-enhancing sequence Step 1. The 5' translation-enhancing sequence (-GCC-GCC-ACC-ATG-G-) (SEQ ID NO:1) was introduced into gene X (a known protein-encoding gene) using a PCR-based method and the following primers:
sense strand (TESX-1) (SEQ ID NO:2):
  5'-GGGG TTT AAG CTT GCC GCC ACC ATG G-(17 nucleotides of gene X)-3'
anti-sense strand (X-3') (SEQ ID NO:3):
  5'-GGGG TTT TCT AGA GGA TCC TCA-(17 nucleotides of gene X)-3'

The primers were combined with dNTPs, Vent DNA polymerase (New England Biolabs) and the template DNA, i.e. gene X in pBluescript (obtained from Stratagene). Five cycles of amplification were carried out, each under the following conditions: 94° C. for 40 seconds, 55° C. for 30 s, and 72° C. for 2 min. This was followed by 20 cycles, each having the following conditions: 94° C. for 40 s, 72° C. for 2.5 min. A single cycle of 72° C. for 10 m followed. The PCR-product and plasmid pBluescript (5 µg) were independently digested with Hind III and Bam HI restrictions enzymes (obtained from New England Biolabs) for 2 hrs. at 37° C. The resulting digestion products were ligated using T4 DNA ligase at 14° C. for 16 hrs. to form a plasmid solution containing a plasmid identified herein as pBSTESX.

Step 2. Following this reaction, E. coli DH5α cells (obtained from Gibco BRL) were transformed with the plasmid solution as follows. Initially, the E. coli DH5α cells were prepared by culturing in 10 ml of 2-YT broth (Molecular Cloning, A Laboratory Manual, 1989) at 37° C. with shaking (200 rpm) for 16 hours. Fresh cultures were initiated at 1:100 dilution and grown at 37° C. until mid-logarithmic phase, i.e. until an absorbance of 0.5 at 550 nm was attained. The cells were collected and resuspended in an ice-cold solution of 50 mM $CaCl_2$ and 10 mM Tris-HCl, pH 8.0, to obtain competent cells.

The cell suspension and the plasmid solution obtained in step 1were combined and kept on ice for 30 minutes and then heated at 42° C. for 2 minutes to introduce the plasmid DNA into the cells. The cell suspension was inoculated in fresh 2-YT broth and cultured at 37° C. for 1 hour with shaking (200 rpm). The cells were spread on 2-YT agar plates containing ampicillin at 100 µg/ml (final concentration), and incubated at 37° C. for about 16 hours to allow selection for ampicillin resistance.

Step 3. Plasmid DNA was isolated from the ampicillin-resistant transformants and prepared as follows. The transformants were precultured in 2-YT media containing ampicillin overnight at 37° C., cultured in 500 ml 2-YT media (1: 100 dilution) at 37° C. for 16 hours and then were centrifuged at a rate of 6,000×g for 15 minutes at 4° C. The cell pellets were retained and resuspended in 50 ml buffer I [50 mM Tris-HCl, 10 mM EDTA, pH 8.0]. This cell suspension was mixed gently with 50 ml buffer II [200 mM NaOH, 1% SDS] at room temperature for 5 minutes in order to lyse the cells. This mixture was combined gently with 50 ml of chilled buffer III [3.0M KAc, pH 5.5] and kept on ice for 30 minutes. The mixture was then centrifuged (20,000×g) for 30 minutes at 4° C. The resulting supernatant was combined with RNase A (100 µg/ml, final concentration) and incubated at room temperature for 30 minutes. This solution was passed through a 0.2µ filter, and then run through a Qiagen tip 2500 column (obtained from Qiagen, Calif., USA). The column was pre-equilibrated with 35 ml of buffer IV [750 mM NaCl, 50 mM MOPS (Sigma), 15% ethanol, pH 7.0, 0.15% Triton X-100], and washed with 4×50 ml of buffer V [1.0M NaCl, 50 mM MOPS, 15% ethanol, pH 7.0]. The solution was eluted with 35 ml of buffer VI [1.25M NaCl, 50 mM Tris-HCl, 15% ethanol, pH 8.5].

The eluent was combined with a 0.7 volume of isopropanol at room temperature and centrifuged (20,000×g) for 30 minutes at 4° C. The resulting pellet was washed with 70% ethanol, and dried under vacuum at room temperature for 5 minutes. The dried pellet was resuspended gently in 1–2 ml sterile deionized distilled water for storage at −20° C. to −80° C.

Step 4. Plasmid pCD-D4.2 (described by Van Tol in Nature, 1992, 358:149, and obtained from Van Tol, Dept. of Pharmacology, University of Toronto) (5 µg), which includes DNA encoding the $D_4$ receptor, was digested with NcoI and BamHI (obtained from New England Biolabs) restriction enzymes at 37° C. for 2 hours. The resulting mixture was electrophoresed through a 1% low melting temperature (LMT) agarose gel to separate the 0.34 kb amino-terminal NcoI-NcoI DNA fragments from the 0.93 kb carboxy-terminal NcoI-BamHI DNA fragments of the $D_4$ receptor. Step 5. Plasmid pBSTESX (5 µg), as prepared in step 1, was also digested with NcoI and BamHI restriction enzymes at 37° C. for 2 hours, and the digested mixture was electrophoresed through a 1% LMT agarose gel. The resulting 2.97 kb NcoI-BamHI DNA fragment, consisting essentially of pBluescript plasmid and synthetic translation-enhancing sequence (identified in step 1), was isolated.

Step 6. The 0.93 kb NcoI-BamHI DNA fragment obtained in step 4 was ligated with the 2.97 kb NcoI-BamHI DNA fragment obtained in step 5 using T4 DNA ligase for 16 hours at 14° C. Following ligation, E. coli DH5α cells were transformed with the ligation product to obtain transformants containing a plasmid identified herein as pBTESD4.2-NcoI. From the transformants thus obtained, plasmid pBTESD4.2-NcoI was prepared as described in step 3.

Step 7. Plasmid pBTESD4.2-NcoI DNA (about 5 µg) was digested with NcoI restriction enzyme at 37° C. for 2 hours. The digestion product was ligated with the 0.34 kb NcoI DNA fragment obtained in step 4 using T4 DNA ligase at 14° C. for 16 hours. Following the ligation reaction, *E. coli* DH5α, prepared as described in step 2, was transformed with ligation product to obtain transformants carrying the plasmid pBTESD4.2. From the transformants thus obtained, the plasmid pBTESD4.2 was prepared (as described in step 3). Once prepared, the orientation of the NcoI DNA fragment in the plasmid was confirmed by a Bst XI restriction enzyme digestion.

Step 8. The $D_4$ coding region, including the inserted 5' translation-enhancing sequence (SEQ ID NO:1) and a native 3' non-coding region, was transferred to the pcDNAI/Amp or pRc/CMV expression vector (available from Invitrogen) as follows. The pcDNAI/Amp or pRc/CMV vector (5 μg) was digested with the HindIII and BamHI (New England Biolabs) restriction enzymes for 2 hours at 37° C. The digestion mixture was electrophoresed through a 1% LMT agarose gel to isolate the desired plasmid fragment.

Plasmid pBTESD4.2 (5 μg), obtained in step 7 above, was also digested with the restriction enzymes HindIII and BamHI at 37° C. for 2 hours, following which the digestion mixture was electrophoresed through a 1% LMT agarose gel. The desired 1.3 kb HindIII-BamHI $D_4$ DNA fragment was isolated.

The purified 1.3 kb and pcDNAI/Amp (or pRc/CMV) DNA fragments were ligated using T4 DNA ligase for 16 hours at 14° C. Following the ligation, *E. coli* DH5α was transformed with the ligation product to obtain transformants containing the desired plasmid pcDThD4.2 (plasmid #1) or pRcThD4.2 product. From the transformants thus obtained, plasmid pcDThD4.2 was prepared as described in step 3. The base sequences at the ligation sites were confirmed by nucleotide sequence analysis as described in Proc. Natl. Acad. Sci. USA, 1977, 74:5463.

Vector containing $D_4$ receptor truncated at 3' non-coding end and a heterologous 5' translation-enhancing sequence Step 9. Plasmid pcDThD4.2 (plasmid #1), or pRcThD4.2, (5 μg) was digested with the restriction enzymes BstXI and XhoI (obtained from New England Biolabs) at 37° C. for 2 hours, the resulting digestion mixture was electrophoresed through a 1% LMT agarose gel, and the desired 5.68 kb BstXI-XhoI DNA fragment (or 6.38 kb BstXI-XhoI DNA fragment consisting of pRc/CMV DNA, synthetic translation-enhancing sequence and the 5' coding sequence of the $D_4$ receptor), consisting essentially of pcDNA1/Amp DNA, synthetic translation-enhancing sequence and the 5' coding sequence of the $D_4$ receptor, was isolated.

Plasmid pBTESD4.2 was PCR-amplified using the DNA primers:
sense strand (HD4-A) (SEQ ID NO:4):
5'-GCCCCCGCCTGTGCGACGCCC-3'; and
anti-sense strand (HD4-3') (SEQ ID NO:5):
5'-GGGGTTTAAGCTTTGCCCGGCTCAGCAGCA GGCACGCA-3'.

PCR was conducted as follows: 5 cycles of amplification at 94° C. for 40 s, 55° C. for 30s, 72° C. for 1.5 min; 20 cycles of 94° C. for 40s, 72° C. for 2 min; and 1 cycle of 72° C. for 10 min. The amplified plasmid mixture was digested with Bst XI at 50° C. for 1 hour and with Hind III at 37° C. for 1 hour, and electrophoresed through a 1% LMT agarose gel, and the 0.79 kb BstXI-HindIII DNA fragment was isolated. The pBluescript vector, also digested with Bst XI and Hind III as described, was ligated with the 0.79 kb BstXI-HindIII DNA fragment using T4 DNA ligase at 14° C. for 16 hours. Following the ligation reaction, *E. coli* DH5α cells were transformed with the reaction product to obtain transformants containing the plasmid pBShD4.2PCR. From the transformant thus obtained, this plasmid was prepared as described in step 3. About 5 μg of the prepared plasmid was then digested with BstXI at 50° C. for 1 hour and XhoI at 37° C. for 1 hour, and electrophoresed through a 1% LMT agarose gel. A desired 0.8 kb BstXI-XhoI DNA fragment was isolated. The 5.68 kb BstXl-XhoI DNA fragment of plasmid pcDThD4.2 (or 6.38 BstXI-Xhol DNA fragment of pRc/CMV ligation product) was ligated with the 0.8 kb BstXI-Xhol DNA fragment using T4 DNA ligase at 14° C. for 16 hours. Following the ligation reaction, *E. coli* DH5α was transformed with the reaction product to obtain transformants containing the plasmid pcDThD4.2-3' (plasmid #2), or plasmid pRcThD4.2-3' (plasmid #3). From the transformants thus obtained, this plasmid was prepared, and the base sequences at the ligated ends of the DNA fragments were confirmed by nucleotide sequence analysis.

Vector containing $D_4$ sequence having native 3' non-coding end and a truncated 5' non-coding end Step 10. The plasmid pBTESD4.2 (5 μg), obtained in step 7, was digested with restriction enzymes SmaI (New England Biolabs) at 30° C. for 1 hour and with XhoI at 37° C. for 1 hour, electrophoresed through a 1% LMT agarose gel and the desired 1.3 kb SmaI-XhoI DNA fragment was isolated.

Plasmid pcDNAI/Amp (Invitrogen) was digested with EcoRV and XhoI, The resulting DNA fragment was reacted with the 1.3 kb SmaI-XhoI DNA fragment (T4 DNA ligase, 14° C., 16 hours). After the ligation reaction, *E. coli* DH5α was transformed with the reaction product to obtain a transformant containing the plasmid pcDhD4.2-SmaI (plasmid #4). From transformants thus obtained, plasmid pcDhD4.2-SmaI was prepared (as described above), and the base sequences at the ligated linking portions of the respective DNA fragments were confirmed by nucleotide sequence analysis (Proc. Natl. Acad. Sci. USA, 74, 5463–5467 (1977)).

EXAMPLE 2

Preparation of Stable Cell lines expressing $D_4$ receptor

CHO Pro-5 cells (ATCC CRL 1281) were transfected with plasmid #3 (containing 5' translation-enhancing sequence (SEQ ID NO:1) in which 3' non-coding region is truncated), using the lipofection method as described below.

To introduce plasmid #3, constructed as described above, the host CHO cells were seeded at a density of 1–2×10⁵ cells/60 mm tissue culture dish in 3 ml 5% FBS-supplemented αMEM medium. After growth for 24 hrs, the medium is removed and the cells are washed once with PBS. Then 3 ml serum-free OPTI-MEM (Reduced-serum medium, Gibco) was added to the cells.

The plasmid DNA-lipofection mix was prepared by combining 50 μl plasmid DNA (3–5 μg) with 30 μl lipofectin (Gibco) and 20 μl of ddH₂O. This mix was let to stand for 15 min. prior to its addition to the cells. On addition, the cell plates were swirled, and incubated overnight in 5% $CO_2$ incubator at 37° C.

Following incubation, the medium was removed from the cell plates, and fresh 5% FBS-supplemented αMEM medium (3 ml) was added. The cells were incubated for 5–6 hours at 37° C., trypsinized, and transferred to tissue culture dishes and fresh 5% FBS-supplemented α-MEM medium (15 ml) was added for overnight incubation at 37° C. in a 5% $CO_2$ incubator. The medium was removed and replaced with fresh medium containing 700 μg G418 (Gibco) per ml. and the cells were again incubated at 37° C. until individual colonies appear. During the incubation period, the medium was changed every 3–4 days.

When colony growth appeared, the cells of the colony were transferred to a 96-well plate and grown to confluence in G418 medium, trypsinized and transferred to a 24 well-plate, grown to confluence, trypsinized and transferred to a 6-well plate, grown to confluence, trypsinized and then transferred to 100 mm or 150 mm tissue culture dishes. G418$^R$ clones were characterized by the use of standard PCR methods, including the use of reverse-transcription PCR (Sambrook et al., Molecular Cloning-A Laboratory Manual, Cold Spring Harbour Laboratory Press, 1989).

HEK 293 cells (ATCC CRL 1573) were also transfected with plasmid pRcThD4.2-3' (plasmid #3) using a lipofection method as described above. In this case, the MEM was supplemented with 10% FBS. Transfectants were selected for by growth in G418-supplemented media. Transfectants were characterized by the PCR techniques mentioned above.

EXAMPLE 3

Ligand Binding Assays

Cell membranes were prepared from 150 mM tissue culture dishes by suspending the cells in assay buffer [50 mM Tris-HCl, pH 7.4 containing 5 mM EDTA, 1.5 mM CaCl$_2$, 5 mM MgCl$_2$, 5 mM KCl, 120 NaCl]. The cells were homogenized using a Teflon pestle. Unbroken cells and nuclei were pelleted at 39,000×g for 15 minutes and the resulting pellet was resuspended in assay buffer at a concentration of 150–250 μg protein/ml.

The cell membrane preparation (about 250 μl, or 50–100 μg protein) was incubated with [$^3$H]Spiperone (0.5–1.0 nM, final concentration) for 2 hours at 22° C. Assays were terminated by washing 3×4 ml with cold 50 mM Tris-HCl, pH 7.4, followed by rapid filtration through a cell harvester and filters were monitored for tritium using the L56000SC (Beckman) counter. Binding data was analyzed using the GRAFIT software package.

Figure 4:
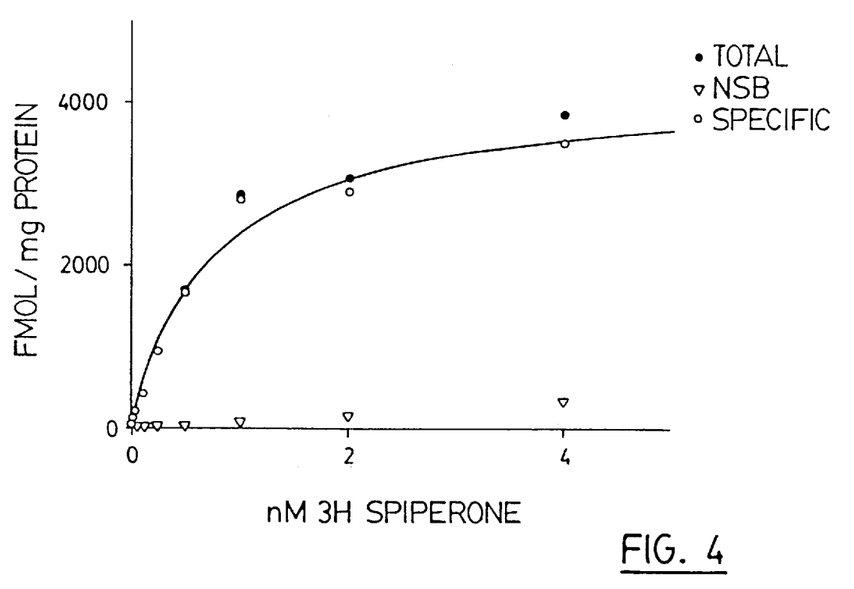
FIG. 4 illustrates the ligand-binding properties of a $D_4$ stable cell line in accordance with the present invention.

Scatchard analysis (FIG. 4) indicated that the stably expressed human D$_4$ receptor contains a single class of [$^3$H]-labelled spiperone binding sites with a dissociation constant (Kd) of about 0.79 nM. Further, the maximum spiperone-binding of the D$_4$ receptor has been found to be 4,344 fmol/mg protein.

EXAMPLE 4

Preparation of Cell lines including plasmids 1, 2 & 4

For the purposes of comparing the expression levels of each modified D$_4$ receptor, COS-1 cells (ATCC CRL 1650) were transfected with the following plasmids obtained as described in Example 1: Plasmid #1 (containing 5' translation-enhancing sequence (SEQ ID NO:1), D$_4$ with native 3' non-coding region), Plasmid #2 (containing 5' translation-enhancing sequence (SEQ ID NO:1), D$_4$ in which 3' non-coding region is truncated) and Plasmid #4 (containing D$_4$ with 3' non-coding region intact).

The DEAE-Dextran transient transfection method was used to introduce the plasmid DNA into the cells. Cells (5×10$^6$/150 mm tissue culture dish) were plated in 15 ml of a DMEM/F12 mixture (1:1 mix of Dulbecco's Modified Eagle Medium and Nutrient Mixture F12) in NaHCO$_3$ (Gibco) supplemented with 10% fetal bovine serum (FBS) and incubated overnight at 37° C. in 5% CO$_2$ incubator. The cells were washed twice with PBS, once with DMEM/F12 with HEPES, pH 7.2 and were then mixed with a transfection mix:

Mix I: 5 ml DMEM/F12 with HEPES, pH 7.2 (Gibco)
    1 ml NuSerum (Collaborative Research Incorporated)
    10 μl chloroquine (100 mM stock) (Fluka Biochemika)
    40 μg plasmid DNA Mix II: 4 ml DMEM/F12 with HEPES, pH 7.2 (Gibco)
    0.4 ml DEAE-Dextran (10 mg/ml stock) (Pharmacia)

Mixes I and II were combined slowly to provide transfection mix. The cells were incubated in 5% CO$_2$ incubator for 3 hours at 37° C., removed from the transfection mix and washed with PBS followed by a wash with DMEM/F12 (with HEPES, pH 7.2). 10 ml 10% DMSO (Sigma) in DMEM/F12 with HEPES, pH 7.2, were added to the cells which were incubated for 1–2 minutes. The solution was removed and the cells were washed twice with PBS and once with DMEM/F2 with HEPES, pH 7.2. This was followed by in cubation for 48–72 hours in 15 ml DMEM/F2 (with NaHCO$_3$) supplemented with 10% FBS. The medium was removed and the cells were washed with cold PBS. The cells were scraped and centrifuged at 800×g for 10 minutes. The pellet could be frozen in liquid N$_2$ for storage at −80° C. Alternatively, the cells can be resuspended in assay buffer [50 mM Tris-HCl, pH 7.4, containing 5 mM EDTA, 1.5 mM CaCl$_2$, 5 mM MgCl$_2$, 5 mM KCl, 120 NaCl] and membrane homogenates prepared as outlined in Example 3.

COS-1 cell membrane (250 μl or 50–100 μg protein) was incubated with [$^3$H]spiperone (0.5–1.0 nM, final concentration) for 2 hours at 22° C. in a total volume of 1.0 ml. Assays were terminated by washing with 3×4 ml cold 50 mM Tris-HCl, pH 7.4 and rapid filtration through a cell harvester and filters were monitored for tritium using the L56000SC (Beckman) counter. Binding d ata were analyzed using GRAFIT.

FIG. 5 shows [$^3$H]Spiperone binding levels of membranes prepared from COS-1 cells transiently transfected with pCD-D4.2 [Nature, 358, 149–152 (1992)], plasmid #1 (pcDThD4-2), plasmid #2 (pcDThD4.2-3'), and plasmid #4 (pcDhD4.2-SmaI). As can be seen, the modifications made to the D$_4$ receptor in accordance with the invention yielded D$_4$ receptor expression plasmids which exhibit at least a 3-fold increase in specific [$^3$H]Spiperone binding sites than has previously been achieved.

---

We claim:

1. A cell line engineered genetically to produce a human $D_4$ receptor, the cells of said cell line having incorporated expressibly into the cellular DNA thereof a construct comprising a nucleotide sequence encoding a human dopamine $D_4$ receptor, wherein said nucleotide sequence is modified at its flanks to incorporate the following:

(1) the 5' non-coding region of SEQ ID NO:9 or SEQ ID NO:12; and (2) a 3' non-coding region of SEQ ID NO:10 or SEQ ID No:11.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
: ( A ) LENGTH: 13 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:1:

GCCGCCACCA TGG 13

( 2 ) INFORMATION FOR SEQ ID NO:2:

( i ) SEQUENCE CHARACTERISTICS:
: ( A ) LENGTH: 26 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:2:

GGGGTTTAAG CTTGCCGCCA CCATGG 26

( 2 ) INFORMATION FOR SEQ ID NO:3:

( i ) SEQUENCE CHARACTERISTICS:
: ( A ) LENGTH: 22 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:3:

GGGGTTTTCT AGAGGATCCT CA 22

( 2 ) INFORMATION FOR SEQ ID NO:4:

( i ) SEQUENCE CHARACTERISTICS:
: ( A ) LENGTH: 21 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:4:

GCCCCCGCCT GTGCGACGCC C 21

( 2 ) INFORMATION FOR SEQ ID NO:5:

( i ) SEQUENCE CHARACTERISTICS:
: ( A ) LENGTH: 38 base pairs
: ( B ) TYPE: nucleic acid
: ( C ) STRANDEDNESS: single
: ( D ) TOPOLOGY: linear ( x i ) SEQUENCE DESCRIPTION: SEQ ID NO:5:

GGGGTTTAAG CTTTGCCCGG CTCAGCAGCA GGCACGCA 38

( 2 ) INFORMATION FOR SEQ ID NO:6:

( i ) SEQUENCE CHARACTERISTICS:
: ( A ) LENGTH: 105 base pairs
: ( B ) TYPE: nucleic acid
: ( C ) STRANDEDNESS: double
: ( D ) TOPOLOGY: linear ( x i ) SEQUENCE DESCRIPTION: SEQ ID NO:6:

ACGCCACCCG CGCCCCGCCT CCCCCAGGAC CCTGCGGCC CCGACTGTGC GCCCCCGCG 60

CCCGGCCTCC CCCCGGACCC CTGCGGCTCC AACTGTGCTC CCCCC 105

( 2 ) INFORMATION FOR SEQ ID NO:7:

```
        ( i ) SEQUENCE CHARACTERISTICS:
                ( A ) LENGTH: 201 base pairs
                ( B ) TYPE: nucleic acid
                ( C ) STRANDEDNESS: double
                ( D ) TOPOLOGY: linear ( x i ) SEQUENCE DESCRIPTION: SEQ ID NO:7:

ACGCCACCCG CGCCCCGCCT CCCCCAGGAC CCCTGCGGCC CCGACTGTGC GCCCCCGCG        60

CCCGGCCTTC CCCGGGGTCC CTGCGGCCCC GACTGTGCGC CCGCCGCGCC CAGCCTCCCC      120

CAGGACCCCT GCGGCCCCGA CTGTGCGCCC CCGCGCCCG GCCTCCCCCC GGACCCCTGC      180

GGCTCCAACT GTGCTCCCCC C                                                201

( 2 ) INFORMATION FOR SEQ ID NO:8:

( i ) SEQUENCE CHARACTERISTICS:
                ( A ) LENGTH: 345 base pairs
                ( B ) TYPE: nucleic acid
                ( C ) STRANDEDNESS: double
                ( D ) TOPOLOGY: linear ( x i ) SEQUENCE DESCRIPTION: SEQ ID NO:8:

ACGCCACCCG CGCCCCGCCT CCCCCAGGAC CCCTGCGGCC CCGACTGTGC GCCCCCGCG        60

CCCGGCCTTC CCCGGGGTCC CTGCGGCCCC GACTGTGCGC CCGCCGCGCC CGGCCTCCCC      120

CCGGACCCCT GCGGCCCCGA CTGTGCGCCC CCGCGCCCG GCCTCCCCA GGACCCCTGC      180

GGCCCCGACT GTGCGCCCCC CGCGCCCGGC CTTCCCCGGG GTCCCTGCGG CCCCGACTGT    240

GCGCCCCCG CGCCCGGCCT CCCCCAGGAC CCCTGCGGCC CCGACTGTGC GCCCCCGCG      300

CCCGGCCTCC CCCCGGACCC CTGCGGCTCC AACTGTGCTC CCCCC                    345

( 2 ) INFORMATION FOR SEQ ID NO:9:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:9:

AAGCTTGCCG CCACCATGG                                                    19

( 2 ) INFORMATION FOR SEQ ID NO:10:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:10:

TGCTGAGCCG GGCA                                                         14

( 2 ) INFORMATION FOR SEQ ID NO:11:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:11:

TGCTGAGCCG GGCAAAGCTT                                                   20

( 2 ) INFORMATION FOR SEQ ID NO:12:
```

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GGGCGCGCCA TGG      13